Sept. 8, 1959 G. VERBEEK Plant Pat. 1,863
ROSE PLANT
Filed Dec. 31, 1958
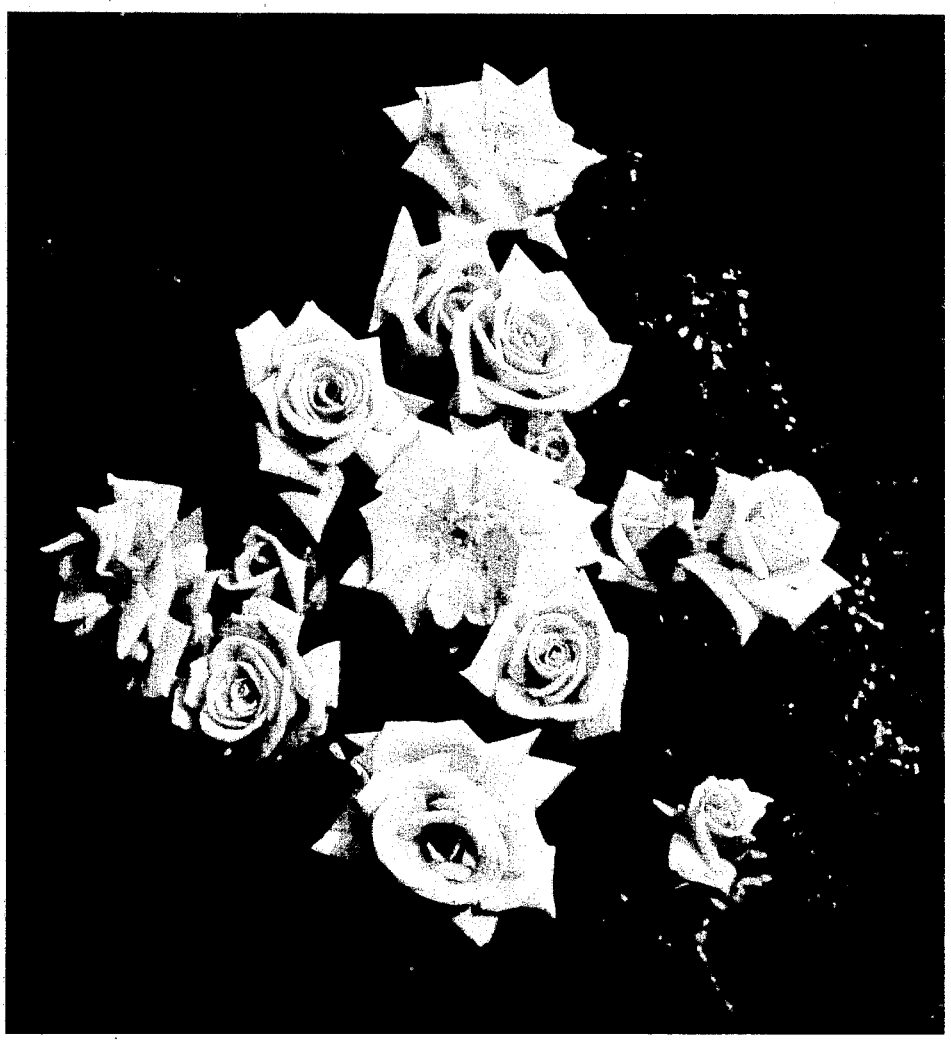
Inventor.
Gysbert Verbeek
By: Robb & Robb
Attorneys.

United States Patent Office

Plant Pat. 1,863

Patented Sept. 8, 1959

1,863

ROSE PLANT

Gysbert Verbeek, Aalsmeer, Netherlands, assignor to Ilgenfritz Nurseries, Inc., Monroe, Mich., a corporation of Michigan Application December 31, 1958, Serial No. 784,412

1 Claim. (Cl. 47—61)

The present invention relates to a new and distinct variety of rose plant of the hybrid floribunda class, which was originated by me by crossing an unnamed and unpatented seedling with the variety "Fashion" (U.S. Plant Patent No. 789).

As the result of this breeding, I have produced a new rose variety which is distinguished from its parents and from all other varieties of its class of which I am aware, and is particularly characterized as to novelty by the following unique combination of outstanding features:

(1) A relatively tall plant habit (taller than "Fashion");

(2) Greater floriferousness than that of "Fashion";

(3) Large blooms (larger than those of "Fashion"); and (4) A distinctive red general color tonality of the flowers which are more red than those of "Fashion."

Asexual reproduction of my new variety by grafting, as performed at Aalsmeer, Holland, shows that the foregoing characteristics and distinctions come true to form and are established and transmitted through succeeding propagations.

The accompanying drawing shows typical specimens of the flowers and foliage of my new variety in different stages of development, and as depicted in color as nearly true as it is reasonably possible to make the same in a color illustration of this character.

The following is a detailed description of the new variety, with color terminology in accordance with the Horticultural Colour Chart issued by the British Colour Council in collaboration with The Royal Horticultural Society, except where general color terms of ordinary dictionary significance are obvious:

Type: Hardy; tall; bush; outdoor; seedling; for garden decoration.

Class: Hybrid floribunda.

Breeding: Seedling.

*Seed parent.*—An unnamed seedling.

*Pollen parent.*—"Fashion."

Propagation: Holds its distinguishing characteristics through succeeding propagations by grafting.

*Flower*

Locality where grown and observed: Aalsmeer, Holland.

Continuity: Continuous.

Fragrance: None.

Flowers borne: Several to stem; in flat clusters; on strong, long stems.

Quantity of bloom: Abundant, outdoors.

Bud:

*Peduncle.*—Short; medium stiffness; smooth. Color—dark red.

*Before calyx breaks.*—Size—medium. Form—pointed; with a conspicuous neck; without foliaceous appendages on the surface of the bud; with slender, cut foliaceous parts extending beyond the tip of the bud equal to ¼ or more of its length. Color—red.

*As calyx breaks.*—Color: inside—Blood Red, Plate 820; outside—blackish, but slightly yellow-tipped at base.

*As first petal opens.*—Size—medium. Form—ovoid. Color: outside—Geranium Lake Red, Plate 20/1; inside—Scarlet Red, Plate 19.

*Opening.*—Opens up well.

Bloom:

*Size (when fully open).*—Medium. Average size when fully expanded—from 2¾ inches to 3½ inches.

*Petalage.*—Double; arranged regularly. Average number of petals under normal conditions—from 16 to 35.

*Form.*—Full and high-centered a first, but becoming flat; petals being at first tightly rolled outward, but later becoming flat and rolled outward at maturity.

Petals:

*Texture.*—Thick; soft.

*Appearance.*—Inside—satiny. Outside—satiny.

*Shape.*—Outside—scalloped. Inside—scalloped.

This description of a newly opened flower was made from a rose grown outdoors in July and August at Aalsmeer, Holland:

*Color.*—Outer petal:—outside surface—Geranium, Plate 20/1; inside surface—Scarlet, Plate 19/1. Intermediate petal:—outside surface—Geranium, Plate 20/1; inside surface—Scarlet, Plate 19/1. Inner petal:—outside surface—Geranium, Plate 20/1; inside surface—Scarlet, Plate 19/1.

This description was made from a rose that was open for 3 days outdoors in the month of August at Aalsmeer, Holland:

*Color.*—Outer petal:—outside surface—Geranium, Plate 20/1; inside surface—Scarlet, Plate 19/1. Inner petal:—outside surface—Geranium, Plate 20/1; inside surface—Scarlet, Plate 19/1.

*General color effect.*—Newly opened flower—Rose Red. 3-days open—Rose Red.

*Behavior.*—Drop off cleanly; slight petal damage in very wet weather.

*Flower longevity.*—On bush in garden—5 days in August and September. Cut roses grown outdoors and kept at living-room temperatures—6 days in July, August and September.

*Reproductive organs*

Stamens: Many, arranged regularly about pistils. Color—yellow.

Filaments: Medium length. Color—yellow.

Anthers: Medium size. Color—yellow.

Pollen: Very abundant.

Pistils: Medium number.

Styles: Medium length.

Stigma: Color—yellow.

Ovaries: Some protruding from calyx.

Hips: Pear-shaped; very smooth; thin walls. Color—yellow.

Sepals: Permanent; long. Color—green.

Seeds: Few; medium size.

*Plant*

Foliage:

*Leaves.*—Compound of 5 leaflets; normal abundance; heavy glossy.

*Leaflets.*—Shape—from oval to ovoid. Base—round.

*Color.*—Mature: upper surface—green; under surface — light green. Young: — upper surface—bronze; under surface—bronze.

*Rachis (the supporting stem of the compound leaf).*—Medium caliper. Upper side—prickly. Under side—prickly.

*Stipules.*—Medium length; narrow.

*Disease resistance.*—Resistant to mildew and blackspot as determined by comparison with other varieties grown under comparable cultural conditions at Aalsmeer, Holland.

Growth:

*Habit.*—Upright.

*Growth.*—Free; vigorous.

*Canes.*—Heavy.

*Main stems.*—Color—bright green. Thorns—few; medium length; straight; narrow base. Prickles—few; color—red. Hairs—none.

*Branches.*—Color—bright green. Thorns—several; medium length; straight; narrow base. Prickles—few; color—reddish. Hairs—none.

*New shoots.* — Color — bronze. Thorns — few; straight; short. Prickles—few; colors—reddish. Hairs—none.

I claim:

A new and distinct variety of rose plant of the hybrid floribunda class, substantially as herein shown and described, characterized particularly as to novelty by the unique combination of a relatively tall plant habit, greater floriferousness than that of the variety "Fashion" (U.S. Plant Patent No. 789), a larger bloom than that of "Fashion," and a distinctive red general color tonality of the flowers, with more red coloring than that of the flowers of "Fashion."

No references cited.